United States Patent [19]

Ohnuma et al.

[11] Patent Number: 5,034,380

[45] Date of Patent: Jul. 23, 1991

[54] ALKOXYMETHYLIDENE EPIPODOPHYLLOTOXIN GLUCOSIDES

[75] Inventors: Takeshi Ohnuma, Tokyo; Takayuki Naito, Kawasaki; Hideo Kamei, Tokyo, all of Japan

[73] Assignee: Bristol-Myers Squibb Company, New York, N.Y.

[21] Appl. No.: 438,829

[22] Filed: Nov. 20, 1989

[51] Int. Cl.$^5$ .................. A61K 31/70; C07H 15/00
[52] U.S. Cl. ........................... 514/27; 536/18.1; 536/17.1; 536/4.1
[58] Field of Search .............. 536/17.1, 18.1, 4.1; 514/27

[56] References Cited

U.S. PATENT DOCUMENTS

| | | | |
|---|---|---|---|
| 4,716,221 | 12/1987 | Umezawa et al. | 536/17.2 |
| 4,904,768 | 2/1990 | Saulnier et al. | 536/17.1 |
| 4,912,204 | 3/1990 | Ohnuma et al. | 536/18.1 |
| 4,916,217 | 4/1990 | Saulnier | 536/17.1 |

FOREIGN PATENT DOCUMENTS 0367189  5/1990  Japan .................. 536/17.1

*Primary Examiner*—Johnnie R. Brown
*Assistant Examiner*—Nancy S. Carson
*Attorney, Agent, or Firm*—Mollie M. Yang

[57] ABSTRACT

Novel cyclic orthoesters and orthocarbonates of 4'-demethylepipodophyllotoxin glucoside are disclosed in the present invention. These compounds are active against experimental murine P388 leukemia.

6 Claims, No Drawings

ALKOXYMETHYLIDENE EPIPODOPHYLLOTOXIN GLUCOSIDES

BACKGROUND OF THE INVENTION

The present invention relates to novel antitumor compounds, their use in inhibiting tumor growth, and pharmaceutical compositions containing them. More particularly, the novel compounds are derivatives of 4'-demethylepipodophyllotoxin glucoside.

Etoposide and teniposide are two derivatives of 4'-demethylepipodophyllotoxin glucoside. The clinical efficacy of etoposide and teniposide in the treatment of a variety of cancers has been well documented and etoposide is currently approved in the United States for the treatment of small cell lung cancer and testicular cancer. The favorable therapeutic and pharmacological profiles of etoposide and teniposide have encouraged much activity in the search for other active analogs within the same class and the research effort of the present inventors in this area has led to the novel analogs disclosed and claimed herein. These new derivatives exhibit good activity against experimental leukemia in animal test models.

SUMMARY OF THE INVENTION

The present invention provides compounds of formula I:

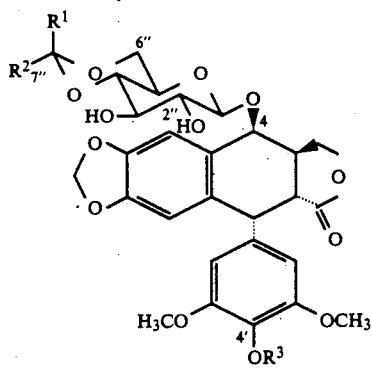

wherein one of $R^1$ and $R^2$ is $C_{1-5}$alkoxy and the other is hydrogen, $C_{1-5}$alkyl, or $C_{1-5}$alkoxy; $R^3$ is hydrogen or $-P(O)(O-M)_2$ wherein M is hydrogen or an alkali metal cation.

Also provided by the present invention are pharmaceutical compositions comprising a compound of formula I and a pharmaceutically acceptable carrier.

Another aspect of the present invention provides a method for inhibiting tumor growth in a mammalian host which comprises administering to said host an antitumor effective dose of a compound of formula I.

DETAILED DESCRIPTION OF THE INVENTION

A preferred embodiment of the present invention provides compounds of formula I wherein one of $R^1$ and $R^2$ is hydrogen and the other is $C_{1-5}$alkoxy. More preferably, the alkoxy group has from one to three carbon atoms.

Another preferred embodiment of the present invention provides compounds of formula I wherein $R^1$ and $R^2$ are the same $C_{1-5}$alkoxy. More preferably, the alkoxy groups have from one to three carbon atoms.

Another preferred embodiment of the present invention provides compounds of formula I wherein $R^3$ is hydrogen.

As used herein the terms "alkyl" and "alkoxy" represent both straight and branched carbon chain; "alkali metal cation" includes lithium, potassium, sodium, and the like.

The starting material 4'-demethyl-4-O$\beta$-D-glucopyranosyl epipodophyllotoxin (hereinafter referred to as DGPE) is known in the art and its preparation is described in, for example, U.S. Pat. No. 3,524,844. The same compound is also readily available from etoposide by acid hydrolysis. The other starting materials, i.e. ortho esters and ortho carbonates are either commercially available or may be prepared according to methods known in the art.

Compounds of formula I wherein $R^3$ is hydrogen are prepared by reacting DGPE with an ortho ester or ortho carbonate of formula II

wherein $R^1$ and $R^2$ are as defined under formula I. and Y is a $C_{1-5}$alkyl group. Suitable ortho esters are for example, trimethyl orthoformate, trimethyl orthoacetate, trimethyl orthobutyrate, and triethyl orthopropionate; and suitable ortho carbonates are for example, tetramethyl orthocarbonate and tetraethyl orthocarbonate. The condensation reaction is carried out in an inert organic solvent such as acetonitrile, methylene chloride, acetone and the like, at a temperature of from about 0° to about 40° C., preferably at about room temperature. The condensation is usually completed after about 1 to about 24 hours. The ortho ester or ortho carbonate reagent is used in at least molar equivalent to the DGPE starting material but it is preferably used in excess relative to DGPE. The reaction is acid catalyzed and suitable acid catalysts are for example a sulfonic acid such as toluenesulfonic acid or camphorsulfonic acid.

The reaction employing a reagent of formula II wherein $R^1$ and $R^2$ are not the same generally affords a mixture containing two desired products: one having $R^1$ in the axial position and $R^2$ in the equatorial position, and the other having $R^2$ in the axial position and $R^1$ in the equatorial position. Thus, for example, using trimethyl orthoformate, the reaction yields one product in which the methoxy is in the axial position (7''-$\beta$-methoxy), and another product in which the methoxy is in the equatorial position (7''-$\alpha$-methoxy). The two isomeric products are separable using conventional separation methods, for example by subjecting the mixture to column chromatography such as $C_{18}$ reversed phase column.

Compounds of formula I thus obtained may be further derivatized to provide the corresponding 4'-phosphate (compounds of formula I wherein $R^3$ is $-P(O)-(O-M)_2$) This may be accomplished by using known methods for converting a hydroxy group into its phosphate ester. Such methods include reacting a compound of formula I wherein $R^3$ is hydrogen with a phosphorylating agent such as phosphorous oxychloride followed by hydrolysis to afford the phosphate product; or reacting the former with diphenyl chlorophosphate followed by catalytic hydrogenation to generate the phosphate ester.

BIOLOGICAL ACTIVITY

Representative compounds of the present invention were evaluated for antitumor activity against murine transplantable P388 leukemia. Female $CDF_1$ mice were inoculated intraperitoneally with approximately $10^6$ P388 leukemic cells (day 0). Test compounds were administered intraperitoneally as a single dose on day 1 and animals were observed for 50 days. The percent increase of median survival time (MST) of treated animals over that of untreated control animals was determined and reported as % T/C. Compounds showing % T/C values of 125 or greater are considered to have significant antitumor activity. Table I shows the results of the in vivo evaluation.

TABLE I

Antitumor Activity Against P388 Leukemia in Mice

| Compound | T/C % of MST[1] | | | | | | | |
|---|---|---|---|---|---|---|---|---|
| | 120[2] | 60 | 30 | 10 | 3 | 1 | 0.3 | 0.1 |
| 1a | 248 | 195 | 166 | 149 | 142 | 137 | 132 | 115 |
| 1b | | | 180 | 165 | 145 | 130 | 120 | 110 |
| 2a | 214 | 181 | 171 | 148 | 133 | 124 | 119 | 114 |
| 2b | 219 (½)[3] | 200 | 167 | 143 | 138 | 119 | 114 | 114 |
| 3 | 210 (⅕) | 170 | 190 | 170 | 140 | 135 | 135 | 125 |
| 4 | 182 | 150 | 145 | 136 | 132 | 127 | 109 | 100 |
| Etoposide | 288 | 212 | 185 | 163 | 143 | 136 | 130 | 120 |

[1]Median survial time.
[2]Dose in mg/kg, QID × 1, ip.
[3]Number of survivors/tested on day 50.

Representative compounds of the present invention were also tested in in vitro cytotoxicity assays against four tumor cell lines. These cell lines were grown and maintained at 37° C. under a humidified atmosphere in a 5% $CO_2$ incubator:

B16-F10 murine melanoma in Eagle's MEM medium (Nissui) containing kanamycin (60 µg/ml) and supplemented with heat-inactivated fetal calf serum (FCS, 10 %) and non-essential amino acids (0.6 %);

Moser human colon carcinoma in Eagle's MEM medium supplemented with FCS (10 %);

K562 human myelogenous leukemia and K562/ADM, an adriamycin-resistant subline which was kindly provided by Dr. Takashi Tsuruo (University of Tokyo) in RPMI 1640 medium (Nissui) supplemented with FCS (10 %), penicillin (100 U/ml) and streptomycin (100 µg/ml).

In experiments using the B16-F10 and Moser cell lines, exponentially growing cells were harvested, counted and suspended in the culture medium at a concentration of $1.5 \times 10^4$ and $3 \times 10^4$ cells/ml, respectively. Twenty-four hours after planting cell suspension (180 µl) into wells of a 96-well microtiter plate, test materials (20 µl) were added to the wells and the plates were incubated for 72 hours. Cytotoxicity against the tumor cells was colorimetrically determined at 540 nm after staining viable cells with neutral red solution. For the K562 and K562/ADM cell lines, 900 µl of the cell suspension ($8 \times 10^4$ cells/ml) was incubated with test materials (100 µl) at 37° C., 5% $CO_2$ for 48 hours in a 24-well tissue culture plate. Cytotoxicity was determined by counting the number of cells using a cell counter. Results of in vitro cytotoxicity assays are shown in Table 2.

TABLE 2

In Vitro Cytotoxicity Against Various Cell Lines

| Compound | $IC_{50}$ (µg/ml) | | | |
|---|---|---|---|---|
| | B16-F10 | Moser | K562 | K562/ADM |
| 1a | 0.094 | ND | ND | ND |
| 1b | 0.27 | 3.4 | ND | ND |
| 2a | 0.11 | 1.7 | 0.065 | >50 |
| 2b | 0.54 | 2.2 | 0.18 | >50 |
| 3 | 2.7 | 3.3 | ND | ND |
| 4 | 7.3 | 3.0 | 0.082 | 32 |

ND = Not Determined

The test results indicate that compounds of the present invention are useful as antitumor compounds. Accordingly, the present invention provides a method for inhibiting mammalian tumors which comprises administering an effective tumor-inhibiting dose of an antitumor compound of formula I to a tumor bearing host. For this purpose, the drug may be administered by conventional routes including, but not limited to, intravenous, intramuscular, intratumoral, intraarterial, intralymphatic, and oral; intravenous administration is preferred.

A further aspect of the present invention provides a pharmaceutical composition which comprises a compound of formula I and a pharmaceutically acceptable carrier. The antitumor composition may be made up of any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

Optimal dosages and regimens for a given mammalian host can be readily ascertained by those skilled in the art. It will, of course, be appreciated that the actual dose used will vary according to the particular composition formulated, the particular compound used, the mode of application and the particular site, host and disease being treated. Many factors that modify the action of the drug will be taken into account including age, weight, sex, diet, time of administration, route of administration, rate of excretion, condition of the patient, drug combinations, reaction sensitivities and severity of the disease.

The following examples are only meant to illustrate the invention and are not to be construed as in any way limiting the scope of the invention which is defined solely by the claims appended to the specification.

PREPARATION OF 4'-DEMETHYL-4-O-β-D-GLUCOPYRANOSYL EPIPODOPHYLLOTOXIN FROM ETOPOSIDE

A mixture of etoposide (5.88 g, 10 mmol) in 30% aqueous acetic acid (100 ml, $AcOH:H_2O = 3:7$) and acetonitrile (50 ml) was refluxed for 9 hours and concentrated in vacuo. The resulting residue was purified by silica gel column chromatography (10% MeOH—$CH_2Cl_2$) to give 2.60 g (51%) of the title compound as colorless crystal. MP 229°–233° C. (lit. 225°–227° C. in Helv. Chim. Acta, 1969, 52:948).

EXAMPLE 1

Preparation of 4'-Demethyl-4-O-(4,6-O-$\beta$-Methoxymethylidene-$\beta$-D-Glucopyranosyl)Epipodophyllotoxin (1a) and 4'-Demethyl-4-O-(4,6-O-$\alpha$-Methoxymethylidene-$\beta$-D-Glucopyranosyl)EpipodophYllotoxin (1b)

To a mixture of 4'-demethyl-4-O-$\beta$-D-glucopyranosyl epipodophyllotoxin (600 mg, 1.1 mmol) and trimethyl orthoformate (1.5 ml) in dichloromethane (60 ml) was added camphorsulfonic acid (85 mg, 0.37 mmol). The reaction mixture was stirred at room temperature for 20 hours, washed with saturated sodium bicarbonate, and dried over $Na_2SO_4$. The solvent was evaporated in vacuo to give 860 mg of a crude oil which was separated by $C_{18}$-reversed phase column chromatography (35% MeOH-H20) to give 292 mg (45%) of 1a as colorless crystals from MeOH and 60 mg (9%) of 1b as colorless crystals from MeOH.

1a:
MP 195°–198° C. Estimated purity 95% by HPLC (LiChrosorb RP-18, 70% MeOH-H$_2$O).
IR $\nu_{max}$ (KBr) cm$^{-1}$ 3400, 1760, 1610.
UV $\lambda_{max}$ (MeOH) nm ($\epsilon$) 240 (sh, 13,300), 284 (4,200).
$^1$H NMR (CDCl$_3$) $\delta$ 5.42 (1H, s, 7''-H), 4.68 (1H, d, J=7.3 Hz, 1''-H), 4.00 (1H, 6, J=10.3 Hz, 6''-Hax), 3.88 (1H, dd, J=5.1 and 9.7 Hz, 6''-Heq), 3.85 (1H, t, J=9.5 Hz, 4''-H), 3.71 (1H, dt, J=2.2 and 9.2 Hz, 3''-H), 3.4-3.5 (2H, m, 2'' and 5''-H), 3.38 (3H, s, 7''-OCH$_3$), 2.64 (1H, d, J=2.2 Hz, 3''-OH), 2.45 (1H, d, J=2.9 Hz, 2''-OH).
Anal. Calcd. for C$_{29}$H$_{32}$O$_{14}$·H$_2$O: C 55.95, H 5.50. Found: C56.11, H 5.33.

1b:
MP 203°–205° C. Estimated purity 85% by HPLC.
IR $\nu_{max}$ (Nujol) cm$^{-1}$ 3350, 1760, 1603.
UV $\lambda_{max}$ (MeOH) nm ($\epsilon$) 240 (13,200), 284 (4,300).
$^1$H NMR (CDCl$_3$) $\delta$5.30 (1H, s, 7''-H), 4.68 (1H, d, J=7.3 Hz, 1''-H), 4.23 (1H, dd, J=4.6 and 10.4 Hz, 6''-Heq), 3.82 (1H, dt, J=2.2 and 8.8 Hz, 3''-H), 3.71 (1H, t, J=10.5 Hz, 6''-Hax), 3.54 (3H, s, 7''-OCH ), 3.46 (1H, t, J=8.8 Hz, 4''-H), 3.4-3.5 (2H, m, 2''and 5''-H), 2.72 (1H, d, J=2.6 Hz, 3''-OH), 2.40 (1H, d, J=2.9 Hz, 2''-OH).
Anal. Calcd. for C$_{29}$H$_{32}$O$_{14}$·H$_2$O: C55.95, H 5.50. Found: C 56.07, H 5.32.

EXAMPLE 2.

Preparation of 4'-Demethyl-4-O-(4,6-O-$\beta$-Ethoxymethylidene-$\beta$-D-Glucopyranosyl)Epipodophyllotoxin (2a) and 4'-Demethyl-4-O-(4,6-O-$\alpha$-Ethoxymethylidene-$\alpha$-D-Glucopyranosyl)Epipodophyllotoxin (2b)

The procedure of Example 1 was repeated using 4'-demethyl-4-O-$\beta$-glucopyranosyl epipodophyllotoxin (1.012 g, 1.8 mmol), triethyl orthoformate (6 ml), and camphorsulfonic acid (60 mg, 0.26 mmol) to give 450 mg (40%) of 2a as colorless crystals from MeOH and 221 mg (19%) of 2b as colorless crystals from MeOH.

2a:
MP 177°–178° C. Estimated purity 90% by HPLC.
IR $\nu_{max}$ (Nujol) cm$^{-1}$ 3380, 1760, 1610.
UV $\lambda_{max}$ (MeOH) nm ($\epsilon$) 240 (13,600), 285 (4,200).
$^1$H NMR (CDCl$_3$) $\delta$5.52 (1H, s, 7''-H), 4.68 (1H, d, J=7.7 Hz, 1''-H), 4.03 (1H, t, J=10.3 Hz, 6''-Hax), 3.87 (1H, t, J=9.5 Hz, 4''-H), 3.86 (1H, dd, J=5.1 and 9.7 Hz, 6''-Heq), 3.71 (1H, dt, J=2.2 and 9.2 Hz, 3''-H), 3.61 (2H, q, J=7.0 Hz, 7''-OCH$_2$CH$_3$), 3.4-3.5 (2H, m, 2''and 5''-H), 2.62 (1H, d, J=2.2 Hz, 3''-OH), 2.43 (1H, d, J=2.6 Hz, 2''-OH), 1.28 (3H, t, J=7.0 Hz, 7''-OCH$_2$CH$_3$).
Anal. Calcd. for C$_{30}$H$_{34}$O$_{14}$·H$_2$O: C56.60, H 5,70. Found: C 56.30, H 5.51.

2b:
MP 168°–171° C. Estimated purity 90% by HPLC.
IR $\nu_{max}$ (Nujol) cm$^{-1}$ 3400, 1770, 1610.
$^1$H NMR (CDCl$_3$) $\delta$ 5.35 (1H, s, 7''-H), 4.68 (1H, d, J=7.7 Hz, 1''-H), 4.22 (1H, dd, J=4.7 and 10.6 Hz, 6''-Heq), 3.82 (2H, q, J=7.3 Hz, 7''-OCH$_2$CH$_3$), 3.70 (1H, t, J=10.3 Hz, 6''-Hax), 3.45 (1H, t, J=9.1 Hz, 4''-H), 3.4-3.5 (2H, m, 2''and 5''-H), 2.73 (1H, d, J=2.2 Hz, 3''-OH), 2.41 (1H, d, J=2.2 Hz, 2''-OH), 1.28 (3H, t, J=7.3 Hz, 7''-OCH$_2$CH$_3$).
Anal. Calcd. for C$_{30}$H$_{34}$O$_{14}$·H$_2$O: C56.60, H 5.70. Found: C 56.31, H 5.43.

EXAMPLE 3.

Preparation of 4'-Demethyl-4-O-(4,6-O-Dimethoxymethylidene-$\beta$-D-Glucopyranosyl)Epipodophyllotoxin (3)

To a mixture of 4'-demethyl-4-O-$\beta$-D-glucopyranosyl epipodophyllotoxin (344 mg, 0.61 mmol) and tetramethyl orthocarbonate (0.5 ml) in tetrahydrofuran (3 ml)-dichloromethane (30 ml) was added camphorsulfonic acid (31 mg, 0.13 mmol). The mixture was stirred at room temperature for 2 hours, washed with saturated sodium bicarbonate, and dried over $Na_2SO_4$. The solvent was evaporated in vacuo to give a crude semisolid, which was purified on a silica gel column (5% MeOH-CH$_2$Cl$_2$) to give 310 mg (80%) of 3 as colorless powder.

3:
MP 170°–173° C. Estimated purity 95% by HPLC.
IR $\nu_{max}$ (KBr) cm$^{-1}$ 3500, 1775, 1610.
UV $\lambda_{max}$ (MeOH) nm ($\epsilon$) 240 (12,600), 284 (4,100).
$^1$H NMR (CDCl$_3$) $\delta$ 4.69 (1H, d, J=7.7 Hz, 1''-H), 4.04 (1H, dd, J=5.3 and 10.1 Hz, 6''-Heq), 3.95 (1H, t, J=10.3 Hz, 6''-Hax), 3.7-3.8 (2H, m, 3'' and 4''-H), 3.46 (3H, s, 7''-OCH$_3$eq), 3.36 (3H, s, 7''-OCH$_3$aq), 3.4-3.5 (2H, m, 2''and 5''-H), 2.63 (1H, d, J=2.1 Hz, 3''-OH), 2.39 (1H, d, J=2.6 Hz, 2''-OH).
Anal. Calcd. for C$_{30}$H$_{34}$O$_{15}$·H$_2$O: C55.21, H 5.56. Found: C 55.63, H 5.43.

EXAMPLE 4

Preparation of 4'-Demethyl-4-O-(4,6-Diethoxymethylidene-$\beta$-D-Glucopvranosyl)Epipodophyllotoxin (4)

The procedure of Example 3 was repeated using 4'-demethyl-4-O-$\beta$-D-glucopyranosyl epipodophyllotoxin (101 mg, 0.18 mmol), tetraethyl orthocarbonate (0.2 ml,, and camphorsulfonic acid (25 mg, 0.11 mmol) to give 81 mg (68%) of 4 as colorless amorphous solid.

4:
MP 152°–156° C. Estimated purity 90% by HPLC.
IR $\nu_{max}$ (KBr) cm$^{-1}$ 3450, 1776, 1610.
UV $\lambda_{max}$ (MeOH) nm ($\epsilon$) 240 (12,700), 285 (4,300).
$^1$H NMR (CDCl$_3$) $\delta$ 4.67 (1H, d, J=7.7 Hz, 1''-H), 4.02 (1H, dd, J=5.9 and 10.4 Hz, 6''-Heq), 3.97 (1H, t, J=10.3 Hz, 6''-Hax), 3.76 (2H, q, J=7.3 Hz, 7''-OCH$_2$CH$_3$eq), 3.74 (1H, t, J=9.5 Hz, 4''-H), 3.65 (2H, q, J=7.3 Hz, 7''-OCH$_2$CH$_3$ax), 3.4-3.5 (2H, m, 2''and 5''-H), 2.64 (1H, d, J=1.8 Hz, 3''-OH), 2.41 (1H, d, J=2.6 Hz, 2''-OH), 1.27 and 1.24 (6H, each t, J=7.0 Hz, 7''-OCH$_2$CH$_3$×2).

Anal. Calcd. for $C_{32}H_{38}O_{15} \cdot \frac{1}{2}H_2O$: C 57.22, H 5.85. Found: C 57.19, H 5.97.

EXAMPLES 5-10

The procedure of Example 1 is followed with the exception that the trimethyl orthoformate used therein is replaced with the ortho esters listed below to afford the corresponding compounds of formula I:

| Ortho Ester | Product of formula I | |
|---|---|---|
| | $R^1$ | $R^2$ |
| triethyl orthoacetate | —$CH_3$ | —$OCH_2CH_3$ |
| | —$OCH_2CH_3$ | —$CH_3$ |
| tripropyl orthoformate | —H | —$O(CH_2)_2CH_3$ |
| | —$O(CH_2)_2CH_3$ | —H |
| triethyl ortho propionate | —$CH_2CH_3$ | —$OCH_2CH_3$ |
| | —$OCH_2CH_3$ | —$CH_2CH_3$ |
| trimethyl orthoacetate | —$CH_3$ | —$OCH_3$ |
| | —$OCH_3$ | —$CH_3$ |
| trimethyl orthobutyrate | —$(CH_2)_2CH_3$ | —$OCH_3$ |
| | —$OCH_3$ | —$(CH_2)_2CH_3$ |
| trimethyl orthovalerate | —$(CH_2)_3CH_3$ | —$OCH_3$ |
| | —$OCH_3$ | —$(CH_2)_3CH_3$ |

What is claimed is:

1. A compound having the formula

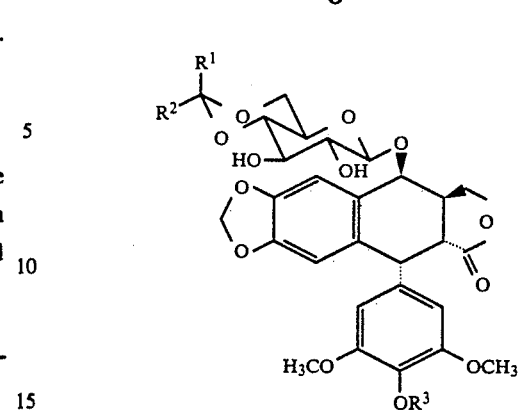

wherein one of $R^1$ and $R^2$ is $C_{1-5}$ alkoxy and the other is selected from the group consisting of hydrogen, $C_{1-5}$ alkyl, and $C_{1-5}$ alkoxy; $R^3$ is hydrogen or -$P(O)(OM)_2$ wherein M is hydrogen or an alkali metal cation.

2. A compound of claim 1 wherein one of $R^1$ and $R^2$ is $C_{1-5}$ alkoxy and the other is H.

3. A compound of claim 1 wherein $R^1$ and $R^2$ are independently $C_{1-5}$ alkoxy.

4. A compound of claim 1 wherein $R^3$ is H; one of $R^1$ and $R^2$ is selected from the group consisting of methoxy and ethoxy, and the other is selected from the group consisting of hydrogen, methoxy, and ethoxy.

5. A compound of claim 1 wherein $R^3$ is H; and $R^1$ and $R^2$ are the same and are selected from the group consisting of methoxy and ethoxy.

6. A pharmaceutical composition which comprises an antitumor effective amount of a compound of claim 1 and a pharmaceutically acceptable carrier.

* * * * *